United States Patent
Iida et al.

(10) Patent No.: US 10,531,661 B2
(45) Date of Patent: Jan. 14, 2020

(54) COATED AGROCHEMICAL GRANULE

(71) Applicant: SUMITOMO CHEMICAL COMPANY, LIMITED, Tokyo (JP)

(72) Inventors: Takahiro Iida, Takarazuka (JP); Kazuyuki Yanagisawa, Tokyo (JP); Ayako Hirao, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/432,586

(22) Filed: Feb. 14, 2017

(65) Prior Publication Data

US 2017/0231222 A1    Aug. 17, 2017

(30) Foreign Application Priority Data

Feb. 16, 2016  (JP) ................. 2016-026627

(51) Int. Cl.
| | |
|---|---|
| *A01N 37/34* | (2006.01) |
| *A01N 25/30* | (2006.01) |
| *A01N 37/02* | (2006.01) |
| *A01N 53/00* | (2006.01) |
| *A01N 25/12* | (2006.01) |
| *A01N 37/38* | (2006.01) |

(52) U.S. Cl.
CPC ............ *A01N 37/34* (2013.01); *A01N 25/12* (2013.01); *A01N 25/30* (2013.01); *A01N 37/02* (2013.01); *A01N 53/00* (2013.01)

(58) Field of Classification Search
CPC ........ A01N 37/34; A01N 53/00; A01N 25/30; A01N 37/02; A01N 25/12; A01N 25/00
See application file for complete search history.

(56) References Cited

U.S. PATENT DOCUMENTS

| | | | | |
|---|---|---|---|---|
| 3,137,618 | A | * | 6/1964 | Pearce ................ A01N 25/26 424/421 |
| 2003/0148887 | A1 | | 8/2003 | Bratz et al. |
| 2009/0263437 | A1 | | 10/2009 | Talmor |
| 2011/0275516 | A1 | | 11/2011 | Wu et al. |
| 2014/0227366 | A1 | | 8/2014 | Zindel et al. |

FOREIGN PATENT DOCUMENTS

| | | |
|---|---|---|
| CN | 102669154 A | 9/2012 |
| CN | 104273120 A | 1/2015 |
| CN | 105409980 A | 3/2016 |
| EP | 1319336 A1 | 6/2003 |
| EP | 1742930 B1 | 7/2008 |
| ES | 2629996 A1 | 8/2017 |
| FR | 3047639 A1 | 8/2017 |
| GB | 2002635 A | 2/1979 |
| HU | E004394 T2 | 2/2005 |
| HU | 229702 B1 | 6/2006 |
| JP | 40-8920 B | 5/1965 |
| JP | 58-124704 A | 7/1983 |
| JP | 2000-86404 A | 3/2000 |
| JP | 2001-253801 A | 9/2001 |
| JP | 2011-246410 A | 12/2011 |
| JP | 2015-63467 A | 4/2015 |
| JP | 2017-145204 A | 8/2017 |
| WO | WO 90/08467 A1 | 8/1990 |
| WO | WO 00/35277 A1 | 6/2000 |
| WO | WO 2006/107905 A1 | 10/2006 |
| WO | WO 2012/146887 A1 | 11/2012 |
| WO | WO 2012/156304 A1 | 11/2012 |

OTHER PUBLICATIONS

Search Report (including an English translation thereof) issued in the corresponding Spanish Patent Application No. 201730179 dated Jun. 26, 2017.
Notification and Search Report (including a partial English translation thereof) issued in the corresponding Polish Patent Application No. P-420555 dated May 13, 2017.
Hungarian Notification and Search Report (including an English translation thereof) issued in the corresponding Hungarian Patent Application No. P1700073 dated Jul. 20, 2017.
Hungarian Notification and Search Report (including an English translation thereof) issued in the corresponding Hungarian Patent Application No. P1700074 dated Jul. 20, 2017.
Spanish Search Report (including an English translation thereof) issued in the corresponding Spanish Patent Application No. 201730178 dated Jun. 7, 2017.
Polish Office Action (including an English translation thereof) issued in the Polish Patent Application No. P.420555 dated Jan. 14, 2019.
French Written Opinion and Preliminary Search Report for French Application No. FR1751229, dated Feb. 14, 2019, with an English translation of the Written Opinion.
Hungarian Office Action, dated Feb. 8, 2019, for Hungarian Application No. P1700073, along with an English translation.
Hungarian Office Action, dated Jan. 30, 2019, for Hungarian Application No. P1700074, along with an English translation.
English translation of HU 229702 B1, published on Jun. 29, 2006.
Hungarian Office Action (including an English translation thereof) issued in the corresponding Hungarian Patent Application No. P1700073 dated Jul. 2, 2018.
Hungarian Office Action (including an English translation thereof) issued in the corresponding Hungarian Patent Application No. P1700074 dated Jul. 2, 2018.

(Continued)

*Primary Examiner* — John Pak
*Assistant Examiner* — Andriae M Holt
(74) *Attorney, Agent, or Firm* — Birch, Stewart, Kolasch & Birch, LLP

(57) ABSTRACT

The present invention provides an agrochemical granule comprising: an oil-non-absorbing carrier; and a layer that coats the oil-non-absorbing carrier, wherein the layer comprises a synthetic pyrethroid compound, an organic solvent whose vapor pressure at 25° C. is equal to or lower than 1.0 Pa, an oil-absorbing carrier, a binding agent, a nonionic surfactant and a dodecylbenzenesulfonate, and having an excellent control efficacy against pest.

3 Claims, No Drawings

(56) References Cited

OTHER PUBLICATIONS

Polish Office Action (including an English translation thereof) issued in the corresponding Polish Patent Application No. P-420555 dated Aug. 2, 2018.
French Written Opinion and Preliminary Search Report, dated Jan. 21, 2019, for French International Application No. 1751228, along with an English translation of the French Written Opinion.
Japanese Notice of Reasons for Refusal (including an English translation thereof) issued in the corresponding Japanese Patent Application No. 2016-026627 dated Nov. 26, 2019.

* cited by examiner

COATED AGROCHEMICAL GRANULE

TECHNICAL FIELD

This application claims priority to and the benefit of Japanese Patent Application Nos. 2016-026627 filed on Feb. 16, 2016, the entire contents of which are incorporated herein by reference.

The present invention relates to a coated agrochemical granule comprising a synthetic pyrethroid compound.

BACKGROUND ART

Hitherto, a synthetic pyrethroid compound has been known as an active ingredient for a pesticide. Also, a coated agrochemical granule wherein an inactive carrier is coated with an agrochemical has been known, and as an example of the coated agrochemical granule, it has been known a granule obtained by coating an inactive carrier having a specific degree of hardness and an oil absorption capacity with an agrochemical such as a pesticide using a binding agent and auxiliaries (see Patent Document 1).

CITATION LIST

Patent Document

Patent Document 1: Japanese Patent Publication No. 40-8920

SUMMARY OF THE INVENTION

Problems to be Solved by Invention

The inventors have been found out that, when the granule obtained by coating an inactive carrier with a synthetic pyrethroid compound is applied to soil for cultivating crops, the control efficacy of the granule against pests is not always sufficient.

An object of the present invention is to provide a coated agrochemical granule comprising a synthetic pyrethroid compound which has an excellent control efficacy against pests.

Means to Solve Problems

The inventors actively studied to find out a coated agrochemical granule comprising a synthetic pyrethroid compound which has an excellent control efficacy against pests, as a result, found out that an agrochemical granule obtained by coating an oil-non-absorbing carrier with a powder that is prepared by mixing a liquid containing a synthetic pyrethroid compound, an organic solvent whose vapor pressure at 25° C. was equal to or lower than 1.0 Pa, a nonionic surfactant, and a dodecylbenzenesulfonate, with an oil-absorbing carrier, has an excellent control efficacy against pests.

That is, the present invention is as follows.
[1] An agrochemical granule comprising:
  an oil-non-absorbing carrier; and
  a layer that coats the oil-non-absorbing carrier, wherein the layer comprises
  a synthetic pyrethroid compound,
  an organic solvent whose vapor pressure at 25° C. is equal to or lower than 1.0 Pa,
  an oil-absorbing carrier,
  a binding agent,
  a nonionic surfactant, and
  a dodecylbenzenesulfonate.
[2] The agrochemical granule as defined in [1], wherein
  a weight ratio of a total of the synthetic pyrethroid compound, the organic solvent whose vapor pressure at 25° C. is equal to or lower than 1.0 Pa, the nonionic surfactant, and the dodecylbenzenesulfonate to the oil-absorbing carrier is within a range of 1:0.3 to 1:2.0.
[3] The agrochemical granule as defined in [1], wherein
  a weight ratio of a total of the synthetic pyrethroid compound, the organic solvent whose vapor pressure at 25° C. is equal to or lower than 1.0 Pa, the nonionic surfactant, and the dodecylbenzenesulfonate to the oil-absorbing carrier is within a range of 1:0.6 to 1:1.5.
[4] The agrochemical granule as defied in any one of [1] to [3], wherein
  the oil-absorbing carrier is an inorganic carrier whose oil absorption amount is equal to or larger than 100 mL/100 g and equal to or smaller than 500 mL/100 g.
[5] The agrochemical granule as defined in any one of [1] to [4], wherein
  the oil-non-absorbing carrier is an inorganic carrier whose oil absorption amount is equal to or larger than 0.01 mL/100 g and equal to or smaller than 20 mL/100 g.
[6] The agrochemical granule according to any one of [1] to [5], wherein
  the oil-absorbing carrier is a synthetic silica.
[7] The agrochemical granule according to any one of [1] to [6], wherein
  the oil-non-absorbing carrier is a silica sand.

The present invention can provide a coated agrochemical granule comprising a synthetic pyrethroid compound which shows an excellent control effect against pests.

MODE FOR CARRYING OUT THE INVENTION

A coated agrochemical granule of the present invention (hereinafter, referred to as "present granule") comprises a synthetic pyrethroid compound. Examples of the synthetic pyrethroid compound include fenvalerate, esfenvalerate, tefluthrin, permethrin, deltamethrin, bifenthrin, cypermethrin, and fenpropathrin. Among these, preferably, bifenthrin, deltamethrin, fenvalerate, esfenvalerate, or fenpropathrin is included, and more preferably, bifenthrin, deltamethrin, esfenvalerate, or fenpropathrin is included.

The content of the synthetic pyrethroid compound in the present granule is within a range of usually 0.1 to 10% by weight and preferably 0.5 to 5% by weight.

The present granule comprises an organic solvent whose vapor pressure at 25° C. is equal to or lower than 1.0 Pa (hereinafter, referred to as "present organic solvent"). Examples of the present organic solvent include bis(2-ethylhexyl) adipate, diisobutyl adipate, triethyl citrate, acetyltriethyl citrate, acetyltributyl citrate, isobutyl oleate, diethyl phthalate, didecyl phthalate, ditridecyl phthalate, diisotridecyl phthalate, soy bean oil, and cotton seed oil. Among these, preferably, triethyl citrate, acetyltributyl citrate, diisotridecyl phthalate, diisobutyl adipate, or cotton seed oil is included. The content of the present organic solvent in the present granule is within a range of usually 0.1 to 20% by weight, preferably 0.5 to 10% by weight, and more preferably 1 to 5% by weight.

The weight ratio of the synthetic pyrethroid compound to the present organic solvent in the present granule is within a range of usually 1:1 to 1:5 and preferably 1:1.3 to 1:3.

The present granule comprises a nonionic surfactant. Examples of the nonionic surfactant include polyoxyethylene alkyl ether, polyoxyethylene alkylaryl ether, polyethylene glycol tris(1-phenylethyl)phenyl ether, polyoxyethylene alkylphenol ether formalin condensate, polyoxyethylene sorbitan fatty acid ester, polyoxyethylene sorbitol fatty acid ester, polyoxyethylene castor oil, polyoxyethylene fatty acid ester, higher fatty acid glycerin ester, sorbitan fatty acid ester, sucrose fatty acid ester, polyoxyethylene polyoxypropylene block polymer, polyoxyethylene fatty acid amide, and polyoxyethylene alkylamine. Among these, preferably, the nonionic surfactant whose HLB value is 10 to 17 is included, and, more preferably, the nonionic surfactant whose HLB value is 13 to 16 is included. The HLB value is defined as a value indicating the degree of the affinity of the surfactant with water and oil. Among these, preferably, polyethylene glycol tris(1-phenylethyl)phenyl ether, polyoxyethylene polyoxypropylene block polymer, or polyoxyethylene castor oil is included.

The content of the nonionic surfactant in the present granule is within a range of usually 0.1 to 5% by weight, preferably 0.2 to 3% by weight, and more preferably 0.3 to 1.5% by weight.

The present granule comprises a dodecylbenzenesulfonate. The dodecylbenzenesulfonate may contain a branched chain. The content of the dodecylbenzenesulfonate in the present granule is within a range of usually 0.1 to 5% by weight, preferably 0.2 to 3% by weight, and more preferably 0.3 to 1.5% by weight.

The weight ratio of the nonionic surfactant to the dodecylbenzenesulfonate in the present granule is within a range of usually 1:0.5 to 1:1.5 and preferably 1:0.8 to 1:1.2.

The present granule comprises an oil-absorbing carrier. The "oil-absorbing carrier" as used herein means an inorganic carrier whose oil absorption amount measured according to the following method is equal to or larger than 100 mL/100 g and, for example, equal to or larger than 100 mL/100 g and equal to or smaller than 500 mL/100 g.

(I) 2.5 g of a specimen is added into a 30 mL polypropylene cylindrical container.

(II) One drop of linseed oil is dripped from a 10 mL burette to the specimen and is mixed with the specimen using a spatula to knead the linseed oil into the specimen. No formation of aggregate composed of the linseed oil and the specimen is confirmed. The linseed oil is a linseed oil whose density measured using a glass pycnometer at 23° C. is within a range of 0.90 to 0.96 (g/mL).

(III) The aforementioned operation of (II) is repeated and the time point at which the aggregate composed of the linseed oil and the specimen is formed is decided to be the ending point.

The oil absorption amount is calculated according to the following equation (1).

$$\text{Oil absorption amount (mL/100 g)} = 100V/2.5 \qquad \text{Eq. (1)}$$

wherein

V: The amount of the linseed oil required for reaching the ending point (mL)

In the present invention, an oil absorbing carrier having a particle size distribution in which the content of particles having the size of 250 μm or more is 1% or less is usually used. The "particle size distribution of the oil absorbing carrier" as used herein means a particle size distribution measured using a sieving method, and "having a particle size distribution in which the content of particles having the size of 250 μm or more is 1% or less" as used herein represents that the weight ratio of the residue amount on a 250 μm aperture sieve relative to the total amount is 1% or less. The particle size distribution of the oil absorbing carrier can be acquired by placing 10 g of the oil absorbing carrier on a 250-μm aperture sieve (a testing sieve that is defined by the Japanese Industrial Standards (JIS) Z8801-1 and whose frame has a diameter of 200 mm and a depth of 45 mm), sieving the oil absorbing carrier for 10 minutes using a sieving apparatus such as a ro-tap shaker, weighing thereafter the weight of the oil absorbing carrier remaining on the sieve, and calculating the particle size distribution by the following equation (2).

$$\text{Residue amount on the sieve (\%)} = \text{Weight of the oil absorbing carrier remaining on the sieve (g)} / \text{Weight of the oil absorbing carrier initially placed on the sieve (g)} \times 100 \qquad \text{Eq. (2)}$$

Examples of the oil absorbing carrier include carbon black (whose oil absorption amount: 110 to 160 mL/100 g) and synthetic silica. Examples of the synthetic silica include wet-process silica (whose oil absorption amount: 210 to 300 mL/100 g) and dry-process silica (whose oil absorption amount: 130 to 190 mL/100 g). Any commercially available oil absorbing carrier can be used as the oil-absorbing carrier. Examples of the commercially available oil absorbing carrier include SIPERNAT 22S (wet-process silica produced by Evonik Industries AG), and AEROSIL R972 (dry-process silica produced by Evonik Industries AG).

The content of the oil absorbing carrier in the present granule is within a range of usually 1 to 10% by weight and preferably 2 to 6% by weight.

The weight ratio of the present organic solvent to the oil-absorbing carrier in the present granule is within a range of usually 1:0.5 to 1:8 and preferably 1:0.8 to 1:4.

The weight ratio of the total of the synthetic pyrethroid compound, the present organic solvent, the nonionic surfactant and the dodecylbenzenesulfonate to the oil-absorbing carrier is within a range of usually 1:0.3 to 1:2.0 and preferably 1:0.6 to 1:1.5.

The present granule comprises an oil-non-absorbing carrier. The "oil-non-absorbing carrier" as used herein means an inorganic carrier whose oil absorption amount measured according to the above method is equal to or smaller than 20 mL/100 g and, for example, equal to or larger than 0.01 mL/100 g and equal to or smaller than 20 mL/100 g.

In the present invention, an oil-non-absorbing carrier having a particle size distribution in which the content of particles having the size of 250 μm or more is 80% or more is usually used. The "particle size distribution of the oil-non-absorbing carrier" as used herein means a particle size distribution measured using a sieving method, and "having a particle size distribution in which the content of particles having the size of 250 μm or more is 80% or more" as used herein represents that the weight ratio of the residue amount on a 250 μm aperture sieve relative to the total amount is 80% or more. The particle size distribution of the oil-non-absorbing carrier can be calculated according to the measurement method of the particle size distribution of the oil-absorbing carrier.

Examples of the oil-non-absorbing carrier include silica sand (whose oil absorption amount: 0.1 to 0.9 mL/100 g), calcium sulfate dihydrate (whose oil absorption amount: 10 to 18 mL/100 g), and zeolite (whose trade name: Izukalite, produced by Neolite Kosan Co., Ltd., whose oil absorption amount: 10 to 15 mL/100 g). Among these, preferably, silica sand is included. The content of the oil-non-absorbing carrier in the present granule is within a range of usually 50 to 99% by weight, preferably 70 to 97% by weight, and more preferably 80 to 95% by weight.

The present granule comprises a binding agent. Examples of the binding agent include Arabian gum, sodium carboxymethylcellulose, hydroxypropylmethylcellulose, methylcellulose, methylethylcellulose, hydroxypropylcellulose, sodium polyacrylate, gam tragacanth, polyvinylpyrolidone, α-starch, polyvinylalcohol, alginic acid, and sodium alginate.

The content of the binding agent in the present granule is within a range of usually 0.1 to 6% by weight and preferably 0.2 to 3% by weight.

The present granule may comprise a coloring agent. Examples of the coloring agent include a pigment and a dye. Among these, preferably, the pigment is included. Examples of the pigment include MONAZOL RED CB EN PASTE (a red pigment produced by BRENNTAG Quimica, S.A.U.).

When the present granule comprises the coloring agent, the content thereof in the present granule is within a range of usually 0 to 3% by weight and preferably 0.1 to 1% by weight.

A production method of the present granule (hereinafter, referred to as "present production method") is described. The present production method comprises a step of mixing the synthetic pyrethroid compound, the present organic solvent, the nonionic surfactant, and the dodecylbenzenesulfonate to prepare a solution (hereinafter, referred to as "step A"), a step of mixing the solution prepared in step A with the oil-absorbing carrier to prepare a powder (hereinafter, referred to as "step B"), and a step of coating the oil-non-absorbing carrier with the powder prepared in step B (hereinafter, referred to as "step C").

In step A, the present organic solvent, the nonionic surfactant, the dodecylbenzenesulfonate, and the synthetic pyrethroid compound that is heated to melt when necessary are mixed. These ingredients are mixed until a uniform mixture is formed to obtain a uniform solution. The mixing operation in step A is performed using a stirrer. Examples of the stirrer include a homogenizer, a propeller stirrer, and the like. When the synthetic pyrethroid compound is heated to melt, the solution is cooled to room temperature.

In step B, the uniform solution prepared in step A and the oil-absorbing carrier are mixed. These ingredients are mixed and can be dry-milled when necessary to obtain a powder. The mixing operation in step B is performed using a mixing machine. Examples of the mixing machine include a ribbon mixer, a Henschel mixer, a nauta mixer, Loedige mixer, and the like. When the dry milling is performed, the milling is performed using a grinder mill. Examples of the grinder mill include a roll mill, a hammer mill, a disk mill, a pin mill, and the like.

In step C, the powder prepared in step B, the oil-non-absorbing carrier, and the binding agent are mixed, or the powder obtained in step B and the oil-non-absorbing carrier are mixed while spraying an aqueous solution of the binding agent to the mixtures. The aqueous solution of the binding agent may comprise the coloring agent. These ingredients can be mixed to coat the oil-non-absorbing carrier with the powder obtained in step B. The mixing operation in step C is performed using a mixing machine. Examples of the mixing machine include the same mixing machines as those used in step B.

After performing step C, a step of drying and sizing the coated granule obtained in step C is performed (hereinafter, referred to as "step D"). The drying operation in step D is performed using a dryer. Examples of the dryer include a hot air dryer, a fluid bed dryer, a rotary dryer, and the like. The drying temperature is within a range of usually 30 to 120° C. and preferably 50° C. to 90° C.

Pests on which the present granule has its control efficacy can be controlled by using the present granule. Examples of the pests include the following pests.
Lepidoptera Pests:
  *Agrotis Ipsilon* and *Agrotis segetum;*
Diptera Pests:
  Root-maggots (*Anthomyiidae* spp.) such as *Delia platura* and *Delia antiqua;*
Coleoptera Pests:
  Corn rootworms (*Diabrotica* spp.) such as western corn rootworm (*Diabrotica virgifera virgifera*) and southern corn rootworm (*Diabrotica undecimpunctata howardi*)),
  Scarab beetles (*Scarabaeidae* spp.) such as *Anomala cuprea, Anomala albopilosa, Anomala rufocuprea,* and *Popillia japonica,*
  Elephant beetles (*Curculionidae* spp.) such as *Sphenophorus uniformis,*
  Click beetles (*Agriotes* spp.).

Examples of the crops applicable by the present granule are as follows.
  crops such as corn, rice, wheat, barley, rye, oat, sorghum, cotton, soybean, peanut, buckwheat, beet, rapeseed, sunflower, sugar cane, and tobacco;
  vegetables such as solanaceous vegetables including eggplant, tomato, pimento, pepper and potato, cucurbitaceous vegetables including cucumber, pumpkin, zucchini, water melon, melon and squash, cruciferous vegetables including Japanese radish, white turnip, horseradish, kohlrabi, Chinese cabbage, cabbage, leaf mustard, broccoli and cauliflower, asteraceous vegetables including burdock, crown daisy, artichoke and lettuce, liliaceous vegetables including green onion, onion, garlic and asparagus, ammiaceous vegetables including carrot, parsley, celery and parsnip, chenopodiaceous vegetables including spinach and Swiss chard, lamiaceous vegetables including *Perilla frutescens,* mint and basil, strawberry, sweet potato, *Dioscorea japonica,* and *colocasia;*
  flowers;
  foliage plants;
  turf grasses;
  fruits such as pomaceous fruits including apple, pear, Japanese pear, Chinese quince and quince, stone fleshy fruits including peach, plum, nectarine, *Prunus mume,* cherry fruit, apricot and prune, citrus fruits including *Citrus unshiu,* orange, lemon, rime and grapefruit, nuts including chestnuts, walnuts, hazelnuts, almond, pistachio, cashew nuts and macadamia nuts, berries including blueberry, cranberry, blackberry and raspberry, grape, kaki fruit, olive, Japanese plum, banana, coffee, date palm, and coconuts; and
  trees other than fruit trees such as tea, mulberry, flowering plant, and roadside trees including ash, birch, dogwood, Eucalyptus, Ginkgo biloba, lilac, maple, *Quercus,* poplar, Judas tree, *Liquidambar formosana,* plane tree, zelkova, Japanese arborvitae, fir wood, hemlock, juniper, *Pinus, Picea,* and *Taxus cuspidata.*

The method for controlling pests using the present granule (hereinafter, referred to as "present control method") comprises a step of applying an effective amount of the present granule to soil where a crop is cultivated (hereinafter, referred to as "step I"). Examples of an application form in step I include an In-furrow application, a side row application, and a pricking-in hole treatment (soil incorporation), and the like.

The application amount of the present granule applied in step I may be varied depending on the kind of the crop, the cultivation conditions for the crop, the timing of the application, the weather conditions, and the like, and which is within a range of usually 5 to 5,000 g and preferably 10 to 2,000 g per 1 hectare of the soil where the crop is cultivated. The present control method can control pests that damage the crop.

Crops can be cultivated in good condition by using the present granule. The method for cultivating a crop using the present granule (hereinafter, referred to as "present cultivation method") comprises step I, and can be carried out in a manner similar to the present control method. The present cultivation method includes an embodiment that comprises a step of seeding or planting of a crop (hereinafter, referred to as "step II"). Preferably, step I is performed concurrently with step II. Examples of the seeding method and the planting method for a crop include those performed using a seeding machine and a transplanting machine. After the seeding or planting of a crop, the crop is cultivated according to the common cultivation method.

EXAMPLES

The present invention is described in more detail below by Examples, but the present invention should not be limited thereto.

Firstly, Preparation Examples and Comparative Preparation Examples are described. Unless otherwise described, the following ingredients in the formulations and apparatuses were used in the Preparation Examples and the Comparative Preparation Examples.

Esfenvalerate: The content of an S-S form: 85.0%, manufactured by Sumitomo Chemical Co., Ltd.

Bifenthrin: Purity: 98.0% or higher, manufactured by Wako Pure Chemical Industries Ltd.

Deltamethrin: Purity: 98.0% or higher, manufactured by Wako Pure Chemical Industries Ltd.

Fenpropathrin: Purity: 93.2% or higher, manufactured by Sumitomo Chemical Co., Ltd.

Proviplast 2624: Acetyltributyl citrate (manufactured by Proviron Industries, the vapor pressure at 25° C. 0.006 Pa)

LINPLAST 13XP: Diisotridecyl phthalate (manufactured by SASOL Germany GmbH, the vapor pressure at 25° C. 0.001 Pa)

Triethyl citrate: Manufactured by Wako Pure Chemical Industries Ltd., the vapor pressure at 25° C. 0.25 Pa Solvesso 200: aromatic hydrocarbons each mainly having 10 to 14 carbon atoms (manufactured by ExxonMobil Chemical, the vapor pressure at 25° C. 5.0 Pa)

Vinycizer 40: Diisobutyl adipate (manufactured by KAO Corporation, the vapor pressure at 25° C. 0.075 Pa)

Cotton seed oil: manufactured by Wako Pure Chemical Industries Ltd., the vapor pressure at 25° C. lower than 1.0 Pa Emulsogen TS290: Polyethylene glycol 2,4,6-tris(1-phenylethyl)phenyl ether (manufactured by Clariant)

Calsogen 4814: calcium linear-dodecylbenzenesulfonate (manufactured by Clariant)

Genapol PF40: Polyoxyethylene polyoxypropylene block polymer (manufactured by Clariant)

Alkamuls 14R: Polyoxyethylene-castor oil (manufactured by Solvay)

SIPERNAT 22S: Wet-process silica (manufactured by Evonik Industries AG)

SUPRAGIL WP: Diisopropylnaphthalene sulfonate (manufactured by Solvay Nicca)

Caolin B-10: Clay (manufactured by INDUSTRIAS FINOR, S.L.)

MOWIOL 4-88: Polyvinyl alcohol (manufactured by KURARAY AMERICA, INC.)

MONAZOL RED CB EN PASTE: A red pigment (manufactured by BRENNTAG Quimica, S.A.U.)

SABBIA P30: Silica sand (manufactured by SIBELCO ITALIA S.P.A.)

Nauta mixer: LV-1, manufactured by Hosokawa Micron Corporation

Preparation Example 1

One point one eight (1.18) parts by weight of esfenvalerate was heated to 60° C. to melt, and 1.88 parts by weight of Proviplast 2624, 0.47 parts by weight of Emulsogen TS290, and 0.47 parts by weight of Calsogen 4814 were then added thereto. The ingredients were mixed until a uniform mixture was formed, and the uniform mixture was cooled to room temperature to prepare a "solution A".

Four point zero zero (4.00) parts by weight of the solution A was added to 3.20 parts by weight of SIPERNAT 22S, and the ingredients were mixed in a mortar for 5 minutes to prepare a "powder A-1".

Zero point zero seven (0.07) parts by weight of SUPRAGIL WP and 0.13 parts by weight of Caolin B-10 were added to 7.20 parts by weight of the powder A-1, and the ingredients were mixed for 1 minute using a juice mixer to prepare a "powder A-2".

A mixture of 11.5 parts by weight of MOWIOL 4-88 and 83.0 parts by weight of ion-exchanged water was heated to 80° C. and was stirred while the temperature was maintained at this temperature to dissolve MOWIOL 4-88 into water, and the resulting solution was cooled to room temperature. Five point five zero (5.50) parts by weight of MONAZOR RED CB EN PASTE was added to the resulting aqueous solution of MOWIOL 4-88, and the ingredients were mixed until a uniform solution was formed to prepare an "aqueous binding agent solution A".

Two point four seven (2.47) parts by weight of the aqueous biding agent solution A was added to 87.66 parts by weight of SABBIA P30 while mixing with a nauta mixer. The mixing operation was continued, and 7.40 parts by weight of the powder A-2 was added portionwise to the mixture of SABBIA P30 and the aqueous binding agent solution A to cause the powder A-2 to adhere to the surface of SABBIA P30. To the resulting mixture, 2.47 parts by weight of the aqueous binding agent solution A was then added and mixed to obtain a coated granule. The coated granule was dried to obtain the granule (1) of the present invention (hereinafter referred to as "Present Granule (1)").

Preparation Example 2

The granule (2) of the present invention (hereinafter referred to as "Present Granule (2)") was obtained by performing the same operations as those of Preparation Example 1 except that 1.02 parts by weight of bifenthrin was used instead of 1.18 parts by weight of esfenvalerate, 1.98 parts by weight of Proviplast 2624 was used instead of 1.88 parts by weight thereof, 0.50 parts by weight of Emulsogen TS290 was used instead of 0.47 parts by weight thereof, and 0.50 parts by weight of Calsogen 4814 was used instead of 0.47 parts by weight thereof.

Preparation Example 3

The granule (3) of the present invention (hereinafter referred to as "Present Granule (3)") was obtained by performing the same operations as those of Preparation Example 1 except that 1.02 parts by weight of deltamethrin was used instead of 1.18 parts by weight of esfenvalerate, 1.98 parts by weight of Proviplast 2624 was used instead of 1.88 parts by weight thereof, 0.50 parts by weight of Emulsogen TS290 was used instead of 0.47 parts by weight thereof, and 0.50 parts by weight of Calsogen 4814 was used instead of 0.47 parts by weight thereof.

Preparation Example 4

The granule (4) of the present invention (hereinafter referred to as "Present Granule (4)") was obtained by performing the same operations as those of Preparation Example 1 except that 1.88 parts by weight of LINPLAST 13XP was used instead of 1.88 parts by weight of Proviplast 2624.

Preparation Example 5

The granule (5) of the present invention (hereinafter referred to as "Present Granule (5)") was obtained by performing the same operations as those of Preparation Example 1 except that 1.88 parts by weight of triethyl citrate was used instead of 1.88 parts by weight of Proviplast 2624.

Preparation Example 6

The granule (6) of the present invention (hereinafter referred to as "Present Granule (6)") was obtained by performing the same operations as those of Preparation Example 1 except that 0.47 parts by weight of Genapol PF40 was used instead of 0.47 parts by weight of Emulsogen TS290.

Preparation Example 7

The granule (7) of the present invention (hereinafter referred to as "Present Granule (7)") was obtained by performing the same operations as those of Preparation Example 1 except that 0.47 parts by weight of Alkamulas 14R was used instead of 0.47 parts by weight of Emulsogen TS290.

Preparation Example 8

The granule (8) of the present invention (hereinafter referred to as "Present Granule (8)") was obtained by performing the same operations as those of Preparation Example 1 except that 1.88 parts by weight of Vinycizer 40 was used instead of 1.88 parts by weight of Proviplast 2624.

Preparation Example 9

The granule (9) of the present invention (hereinafter referred to as "Present Granule (9)") was obtained by performing the same operations as those of Preparation Example 1 except that 1.88 parts by weight of the cotton seed oil was used instead of 1.88 parts by weight of Proviplast 2624.

Preparation Example 10

One point zero zero (1.00) parts by weight of fenpropathrin was heated to 60° C. to melt, and 1.95 parts by weight of Proviplast 2624, 0.49 parts by weight of Genapol PF40, and 0.49 parts by weight of Calsogen 4814 were then added thereto. The ingredients were mixed until a uniform mixture was formed, and the uniform mixture was cooled to room temperature to prepare a solution. The same succeeding operations as those of Preparation Example 1 were thereafter performed to obtain the granule (10) of the present invention (hereinafter referred to as "Present Granule (10)").

Preparation Example 11

The granule (11) of the present invention (hereinafter referred to as "Present Granule (11)") was obtained by performing the same operations as those of Preparation Example 10 except that 0.49 parts by weight of Alkamuls 14R was used instead of 0.49 parts by weight of Genapol PF 40.

Comparative Preparation Example 1

The comparative granule (1) was obtained by performing the same operations as those of Preparation Example 1 except that 2.35 parts by weight of Proviplast 2624 was used instead of 1.88 parts by weight thereof and 0.47 parts by weight of Emulsogen TS290 was not used.

Comparative Preparation Example 2

The comparative granule (2) was obtained by performing the same operations as those of Preparation Example 1 except that 0.94 parts by weight of Calsogen 4814 was used instead of 0.47 parts by weight thereof and 0.47 parts by weight of Emulsogen TS290 was not used.

Comparative Preparation Example 3

The comparative granule (3) was obtained by performing the same operations as those of Preparation Example 1 except that 2.35 parts by weight of Proviplast 2624 was used instead of 1.88 parts by weight thereof and 0.47 parts by weight of Calsogen 4814 was not used.

Comparative Preparation Example 4

The comparative granule (4) was obtained by performing the same operations as those of Preparation Example 1 except that 0.94 parts by weight of Emulsogen TS290 was used instead of 0.47 parts by weight thereof and 0.47 parts by weight of Calsogen 4814 was not used.

Comparative Preparation Example 5

The comparative granule (5) was obtained by performing the same operations as those of Preparation Example 1 except that 2.82 parts by weight of Proviplast was used instead of 1.88 parts by weight thereof, and neither 0.47 parts by weight of Calsogen 4814 nor 0.47 parts by weight of Emulsogen TS290 were used.

Comparative Preparation Example 6

The comparative granular formulation (6) was obtained by performing the same operations as those of Preparation Example 1 except that 1.88 parts by weight of Solvesso 200 was used instead of 1.88 parts by weight of Proviplast 2624.

Comparative Preparation Example 7

One point zero zero (1.00) parts by weight of fenpropathrin was heated to 60° C. to melt, and 2.93 parts by weight of Proviplast 2624 was then added thereto. The ingredients were mixed until a uniform mixture was formed and the uniform mixture was cooled to room temperature to prepare a solution. The same succeeding operations as those of Preparation Example 1 were thereafter performed to obtain the comparative granular formulation (7).

Next, test Examples are described.

Test Example 1

Soil was packed in a plastic container having a longitudinal length of 15 cm, a lateral length of 20 cm, and a depth of 7 cm, and a furrow having a length of 15 cm and a depth of 3 cm was formed to have a V-shape in a direction perpendicular to the surface of the soil. One (1) grain of corn seed was placed in the furrow, and the granule was applied to the inside of the furrow so that the application rate of the synthetic pyrethroid compound per area of the soil in the container would be 120 g/ha, and the furrow was closed by placing the soil of a furrow side on the furrow. This corn was cultivated in a greenhouse.

Ten (10) days after the application of the granule, 20 newly hatched larvae of western corn rootworm (*Diabrotica virgifera virgifera*) were released per one corn plant. This was called "treated plot".

On the other hand, corn was cultivated in a manner similar to those of the treated plot except that the granule was not applied, and 20 newly hatched larvae of *Diabrotica virgifera virgifera* were released. This was called "untreated plot".

Ten (10) days after the release of the insects, the corn plants were collected, and the insect damage caused by the newly hatched larvae of *Diabrotica virgifera virgifera* to the corn nodal roots was visually examined, and the ratio of the number of damaged nodal roots to the number of all the nodal roots was calculated as a damage ratio according to the following Equation (3).

Damage ratio (%)=100×$A/B$     Eq. (3)

wherein

A: Number of damaged nodal roots

B: Number of all the nodal roots

The preventive value was calculated according to the following equation (4) and an average preventive value of 5 repetitions was then determined.

Preventive value (%)=100×(1−$C/D$)     Eq. (4)

wherein

C: Damage ratio of the treated plot

D: Damage ratio of the untreated plot

The result is shown in Table 1.

TABLE 1

| Applied Granule | Preventive Value (%) |
|---|---|
| Present Granule (1) | 89.9 |
| Present Granule (2) | 60.0 |
| Present Granule (3) | 76.4 |
| Present Granule (4) | 74.3 |
| Present Granule (5) | 85.4 |
| Comparative Granule (1) | 28.0 |
| Comparative Granule (2) | 37.6 |
| Comparative Granule (3) | 9.0 |
| Comparative Granule (4) | 11.5 |
| Comparative Granule (5) | 10.1 |
| Comparative Granule (6) | 31.1 |

Test Example 2

Soil was packed in a plastic container having a longitudinal length of 15 cm, a lateral length of 20 cm, and a depth of 7 cm, and a furrow having a length of 15 cm and a depth of 3 cm was formed to have a V-shape in a direction perpendicular to the surface of the soil. One (1) grain of corn seed was placed in the furrow, and the granule was applied to the inside of the furrow so that the application rate of the synthetic pyrethroid compound per area of the soil in the container would be 144 g/ha, and the furrow was closed by placing the soil of a furrow side on the furrow. This corn was cultivated in a greenhouse.

Twenty (20) days after the application of the granule, 25 newly hatched larvae of western corn rootworm (*Diabrotica virgifera virgifera*) were released per one corn plant. This was called "treated plot".

On the other hand, corn was cultivated in a manner similar to those of the treated plot except that the granule was not applied, and 25 newly hatched larvae of *Diabrotica virgifera virgifera* were released. This was called "untreated plot".

Ten (10) days after the release of the insects, the corn plants were collected, and the insect damage caused by the newly hatched larvae of *Diabrotica virgifera virgifera* to the corn nodal roots was visually examined, and the ratio of the number of damaged nodal roots to the number of all the nodal roots was calculated as a damage ratio according to the Eq. (3) described above in Test Example 1 and an average preventive value of 5 repetitions was then determined according to the equation (4) described above in Test Example 1.

The result is shown in Table 2.

TABLE 2

| Applied Granule | Preventive Value (%) |
|---|---|
| Present Granule (1) | 100 |
| Present Granule (6) | 93.4 |
| Present Granule (7) | 94.0 |
| Present Granule (8) | 72.0 |
| Present Granule (9) | 66.4 |
| Present Granule (10) | 88.7 |
| Present Granule (11) | 70.9 |
| Comparative Granule (5) | 45.7 |
| Comparative Granule (7) | 42.4 |

The invention claimed is:

1. An agrochemical granule comprising:
   70 to 97% by weight of a silica sand; and
   a layer that coats the silica sand, wherein
   the layer comprises
   0.1 to 10% by weight of a synthetic pyrethroid compound selected from the group consisting of fenvalerate, esfenvalerate, permethrin, deltamethrin, bifenthrin, cypermethrin and fenpropathrin,
   0.1 to 20% by weight of an organic solvent wherein the vapor pressure of the organic solvent at 25° C. is equal to or lower than 1.0 Pa,
   1 to 10% by weight of a synthetic silica,
   0.1 to 6% by weight of a binding agent,
   0.1 to 5% by weight of a nonionic surfactant wherein the HLB value of the nonionic surfactant is 13 to 16, and
   0.1 to 5% by weight of dodecylbenzenesulfonate.

2. The agrochemical granule according to claim 1, wherein
   a weight ratio of a total of the synthetic pyrethroid compound, the organic solvent whose vapor pressure at 25° C. is equal to or lower than 1.0 Pa, the nonionic surfactant, and the dodecylbenzenesulfonate to the synthetic silica is within a range of 1:0.3 to 1:2.0.

3. The agrochemical granule according to claim 1, wherein a weight ratio of a total of the synthetic pyrethroid compound, the organic solvent whose vapor pressure at 25° C. is equal to or lower than 1.0 Pa, the nonionic surfactant, and the dodecylbenzenesulfonate to the synthetic silica is within a range of 1:0.6 to 1:1.5.

* * * * *